(12) United States Patent
Pacetti et al.

(10) Patent No.: US 9,901,663 B2
(45) Date of Patent: Feb. 27, 2018

(54) HOLLOW STENT FILLED WITH A THERAPEUTIC AGENT FORMULATION

(71) Applicant: Abbott Cardiovascular Systems Inc., Santa Clara, CA (US)

(72) Inventors: Stephen D. Pacetti, San Jose, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 24 days.

(21) Appl. No.: 14/267,620

(22) Filed: May 1, 2014

(65) Prior Publication Data

US 2014/0330365 A1 Nov. 6, 2014

Related U.S. Application Data

(60) Provisional application No. 61/820,155, filed on May 6, 2013.

(51) Int. Cl.
| | |
|---|---|
| *A61F 2/82* | (2013.01) |
| *A61L 31/14* | (2006.01) |
| *A61L 31/02* | (2006.01) |
| *A61L 31/16* | (2006.01) |
| *B65B 3/00* | (2006.01) |

(Continued)

(52) U.S. Cl.
CPC ............... *A61L 31/16* (2013.01); *A61F 2/82* (2013.01); *A61L 27/505* (2013.01); *A61L 31/022* (2013.01); *A61L 31/143* (2013.01); *B65B 3/003* (2013.01); *A61F 2250/0067* (2013.01); *A61F 2250/0068* (2013.01); *A61L 27/50* (2013.01); *A61L 27/54* (2013.01); *A61L 2300/00* (2013.01); *A61L 2300/416* (2013.01); *A61L 2300/426* (2013.01); *A61L 2300/604* (2013.01); *A61L 2300/802* (2013.01); *Y10T 29/49993* (2015.01)

(58) Field of Classification Search
None
See application file for complete search history.

(56) References Cited

U.S. PATENT DOCUMENTS

| | | | |
|---|---|---|---|
| 3,429,717 | A | 2/1969 | Cook |
| 3,993,622 | A | 11/1976 | Brunetti |

(Continued)

FOREIGN PATENT DOCUMENTS

| | | |
|---|---|---|
| EP | 0 850 651 | 1/1998 |
| EP | 0 875 218 | 4/1998 |

(Continued)

OTHER PUBLICATIONS

International Search Report for PCT/US2014/036427, dated Jul. 24, 2014, 13 pgs.

(Continued)

*Primary Examiner* — Leslie Lopez
(74) *Attorney, Agent, or Firm* — Squire Patton Boggs (US) LLP

(57) ABSTRACT

A composition for loading into a structural element of a stent, where the structural element is defined by a lumen and at least one opening to access the lumen. The composition may comprise a therapeutic agent, and a chelator, a precipitation agent, or a combination thereof. Medical devices, such as stents, with a structural element defined by a lumen and at least one opening to access the lumen, filled with the compositions are also described.

25 Claims, 2 Drawing Sheets

(51) Int. Cl.
*A61L 27/50* (2006.01)
*A61L 27/54* (2006.01)

(56) References Cited

U.S. PATENT DOCUMENTS

| | | |
|---|---|---|
| 4,401,804 A | 8/1983 | Wooten et al. |
| 4,459,252 A | 7/1984 | MacGregor |
| 5,006,281 A | 4/1991 | Rubin et al. |
| 5,059,211 A | 10/1991 | Stack et al. |
| 5,163,952 A | 11/1992 | Froix |
| 5,288,711 A | 2/1994 | Mitchell et al. |
| 5,306,286 A | 4/1994 | Stack et al. |
| 5,344,425 A | 9/1994 | Sawyer |
| 5,527,337 A | 6/1996 | Stack et al. |
| 5,539,081 A | 7/1996 | Gruber et al. |
| 5,581,387 A | 12/1996 | Cahill et al. |
| 5,618,866 A | 4/1997 | Prabhu et al. |
| 5,700,286 A | 12/1997 | Tartaglia et al. |
| 5,713,949 A | 2/1998 | Jayaraman |
| 5,766,710 A | 6/1998 | Turnland et al. |
| 5,769,883 A | 6/1998 | Buscemi et al. |
| 5,843,172 A | 12/1998 | Yan |
| 5,873,904 A | 2/1999 | Ragheb et al. |
| 5,902,266 A | 5/1999 | Leone et al. |
| 5,972,027 A | 10/1999 | Johnson |
| 5,992,000 A | 11/1999 | Humphrey et al. |
| 6,037,022 A | 3/2000 | Adur et al. |
| 6,065,597 A | 5/2000 | Petterson et al. |
| 6,120,536 A | 9/2000 | Ding et al. |
| 6,120,847 A | 9/2000 | Yang et al. |
| 6,206,915 B1 | 3/2001 | Fagan et al. |
| 6,264,596 B1 | 7/2001 | Weadock |
| 6,287,628 B1 | 9/2001 | Hossainy et al. |
| 6,309,383 B1 | 10/2001 | Campbell et al. |
| 6,379,381 B1* | 4/2002 | Hossainy ............... A61L 31/146 623/1.15 |
| 6,478,776 B1 | 11/2002 | Rosenman et al. |
| 6,485,950 B1 | 11/2002 | Kumar et al. |
| 6,497,916 B1 | 12/2002 | Taylor et al. |
| 6,506,437 B1* | 1/2003 | Harish ................... A61L 31/10 427/2.25 |
| 6,592,814 B2 | 7/2003 | Wilcox et al. |
| 6,608,187 B2 | 8/2003 | Nelson et al. |
| 6,623,519 B2 | 9/2003 | Edwin et al. |
| 6,727,300 B2 | 4/2004 | Sassi |
| 6,746,622 B2 | 6/2004 | Yang et al. |
| 6,875,400 B2 | 4/2005 | Speer |
| 6,949,254 B2 | 9/2005 | Gen |
| 7,022,258 B2 | 4/2006 | Yang et al. |
| 7,192,395 B1 | 3/2007 | Qu et al. |
| 7,335,391 B1 | 2/2008 | Pacetti et al. |
| 7,704,518 B2 | 4/2010 | Tamarkin et al. |
| 7,785,647 B2 | 7/2010 | Ding |
| 7,901,726 B2 | 3/2011 | McMorrow et al. |
| 8,007,737 B2 | 8/2011 | Fennimore, Jr. |
| 8,076,137 B2 | 12/2011 | McAllister et al. |
| 8,124,166 B2 | 2/2012 | Owens et al. |
| 8,128,688 B2 | 3/2012 | Ding et al. |
| 8,182,527 B2 | 5/2012 | Llanos et al. |
| 8,207,240 B2 | 6/2012 | Lambert et al. |
| 8,394,446 B2 | 3/2013 | Ding |
| 2002/0015542 A1 | 2/2002 | Bradley |
| 2002/0022144 A1 | 2/2002 | Yang et al. |
| 2002/0055769 A1 | 5/2002 | Wang |
| 2002/0081228 A1 | 6/2002 | Hui et al. |
| 2002/0153511 A1 | 10/2002 | Cotterman |
| 2003/0083646 A1 | 5/2003 | Sirhan et al. |
| 2003/0144145 A1 | 7/2003 | Yang et al. |
| 2003/0181975 A1* | 9/2003 | Ishii ...................... A61L 31/10 623/1.42 |
| 2003/0189192 A1 | 10/2003 | Girelli et al. |
| 2003/0204239 A1 | 10/2003 | Carlyle et al. |
| 2003/0215564 A1 | 11/2003 | Heller et al. |
| 2003/0216806 A1 | 11/2003 | Togawa et al. |
| 2004/0009229 A1 | 1/2004 | Unger et al. |
| 2004/0033269 A1 | 2/2004 | Hei et al. |
| 2004/0086542 A1 | 5/2004 | Hossainy |
| 2004/0116332 A1 | 6/2004 | Ornberg et al. |
| 2004/0133270 A1 | 7/2004 | Grandt |
| 2004/0220660 A1 | 11/2004 | Shanley et al. |
| 2005/0004663 A1* | 1/2005 | Llanos ................... A61L 31/16 623/1.46 |
| 2005/0037048 A1 | 2/2005 | Song |
| 2005/0048121 A1* | 3/2005 | East ...................... A61K 9/0024 424/486 |
| 2005/0182390 A1 | 8/2005 | Shanley |
| 2006/0115514 A1* | 6/2006 | Gengrinovitch ........ A61L 27/54 424/423 |
| 2006/0224234 A1* | 10/2006 | Jayaraman ................ A61F 2/86 623/1.16 |
| 2006/0246109 A1* | 11/2006 | Hossainy ................ A61L 31/10 424/426 |
| 2006/0276879 A1 | 12/2006 | Lye et al. |
| 2007/0043423 A1 | 2/2007 | Grewe |
| 2007/0110891 A1 | 5/2007 | Pacetti |
| 2007/0141112 A1 | 6/2007 | Falotico et al. |
| 2007/0173923 A1 | 7/2007 | Savage et al. |
| 2007/0198080 A1 | 8/2007 | Ding et al. |
| 2007/0224244 A1 | 9/2007 | Weber et al. |
| 2007/0241286 A1 | 10/2007 | Greenwald et al. |
| 2007/0258903 A1 | 11/2007 | Kleiner et al. |
| 2007/0259101 A1 | 11/2007 | Hossainy et al. |
| 2008/0026034 A1 | 1/2008 | Cook et al. |
| 2008/0118734 A1* | 5/2008 | Goodwin ................ B05D 1/62 428/221 |
| 2008/0188836 A1 | 8/2008 | Weber et al. |
| 2008/0195189 A1 | 8/2008 | Asgari |
| 2008/0255659 A1 | 10/2008 | Huang et al. |
| 2009/0061071 A1 | 3/2009 | McMorrow et al. |
| 2009/0118819 A1 | 5/2009 | Merz et al. |
| 2009/0132031 A1 | 5/2009 | Cook et al. |
| 2009/0287300 A1 | 11/2009 | Dave et al. |
| 2009/0319031 A1 | 12/2009 | Wang et al. |
| 2009/0319032 A1 | 12/2009 | Weber et al. |
| 2010/0010621 A1* | 1/2010 | Klocke ...................... A61F 2/82 623/1.16 |
| 2010/0036047 A1 | 2/2010 | Janowicz et al. |
| 2010/0076546 A1 | 3/2010 | Dias et al. |
| 2010/0300903 A1 | 12/2010 | Ding |
| 2010/0300917 A1 | 12/2010 | Ding |
| 2011/0070357 A1* | 3/2011 | Mitchell ................ A61L 31/16 427/2.25 |
| 2011/0190876 A1 | 8/2011 | Zhao |
| 2011/0245332 A1 | 10/2011 | Falotico et al. |
| 2011/0294998 A1 | 12/2011 | Davis et al. |
| 2012/0067454 A1 | 3/2012 | Melder et al. |
| 2012/0077851 A1* | 3/2012 | Zhang .................... C07D 213/81 514/346 |
| 2012/0674540 | 3/2012 | Melder et al. |
| 2012/0216905 A1 | 8/2012 | Pacetti |
| 2012/0216907 A1 | 8/2012 | Pacetti |
| 2012/0216908 A1 | 8/2012 | Pacetti |
| 2012/0216912 A1 | 8/2012 | Pacetti |
| 2012/0216913 A1 | 8/2012 | Pacetti |
| 2012/0216914 A1 | 8/2012 | Pacetti |
| 2012/0216916 A1 | 8/2012 | Pacetti |
| 2012/0219696 A1 | 8/2012 | Pacetti |
| 2013/0004425 A1 | 1/2013 | Wang et al. |
| 2013/0085166 A1* | 4/2013 | Makra .................... A61K 31/215 514/352 |
| 2013/0145729 A1 | 6/2013 | Ding |
| 2013/0150953 A1 | 6/2013 | Ding |
| 2013/0276412 A1 | 10/2013 | Pacetti |
| 2014/0102049 A1 | 4/2014 | Pacetti et al. |
| 2014/0238535 A1 | 8/2014 | Pacetti |
| 2014/0246120 A1 | 9/2014 | Pacetti |

FOREIGN PATENT DOCUMENTS

| | | |
|---|---|---|
| EP | 0932399 | 8/1999 |
| EP | 1827528 | 9/2007 |
| EP | 2059272 A1 | 5/2009 |
| EP | 2533764 | 12/2012 |

(56) References Cited

FOREIGN PATENT DOCUMENTS

| | | |
|---|---|---|
| JP | 11-299901 | 11/1999 |
| JP | 2003-253031 | 9/2003 |
| WO | WO 90/01969 | 3/1990 |
| WO | WO 97/33552 | 9/1997 |
| WO | WO 98/23228 | 6/1998 |
| WO | WO 98/41559 | 9/1998 |
| WO | WO 99/16386 | 4/1999 |
| WO | WO 99/22670 | 5/1999 |
| WO | WO 01/04117 | 1/2001 |
| WO | WO 01/90202 | 11/2001 |
| WO | WO 03/045582 | 6/2003 |
| WO | WO 03/053171 | 7/2003 |
| WO | WO 2004/050795 | 6/2004 |
| WO | WO 2004/087214 | 10/2004 |
| WO | WO 2005/016399 | 2/2005 |
| WO | WO 2006/020742 | 2/2006 |
| WO | WO 2006/056984 | 6/2006 |
| WO | WO 2006/082221 | 8/2006 |
| WO | WO 2006/089499 | 8/2006 |
| WO | WO 2007/005910 | 1/2007 |
| WO | WO 2007/021749 | 2/2007 |
| WO | WO 2008/031596 | 3/2008 |
| WO | WO 2008/098926 | 8/2008 |
| WO | WO 2008/098927 | 8/2008 |
| WO | WO 2009/117241 | 9/2009 |
| WO | WO 2011/097563 | 8/2011 |
| WO | WO 2012/038881 | 3/2012 |

OTHER PUBLICATIONS

"Medtronic non-polymeric DES development: from nanoporous coatings to drug filled tubes", Medtronic presentation, 32 pgs (2010).

Chelate science definition, downloaded from: www.science.yourdictionary.com/chelate, Apr. 23, 2013 1 pg.

Chelate, definition in free online dictionary, 2 pgs. downloaded from: www.thefreedictionary.com/chelator, Apr. 23, 2013, 2 pgs.

DuPont, Freon 11, http://www.dupont.com/msds/40_37_2090fr.html, printed Feb. 21, 2002, 8 pages.

DuPont, Freon 113 Refrigerant, Material Safety Data Sheet, revised Apr. 20, 2004, 8 pages.

DuPont, Freon 12, Material Safety Data Sheet, revised Apr. 19, 2004, 7 pages.

DuPont, Freon: Thermodynamic Properties of DuPont™ Freon® 22 (R-22) Refrigerant.

Han et al., titled: Density, Viscosity, and Excess Properties for Aqueous Poly(ethylene glycol) Solutions from (298.15 to 323.15) K, 2008.

Liggins et al., "Solid-State Characterization of paclitaxel", J. of Pharm. Sciences vol. 86, No. 12, pp. 1458-1463 (1997).

MAYZO "BNX® MD-1024 Antioxidant & Metal Deactivator", product data sheet, 3 pgs. (2005).

Perry's Chemical Engineers' Handbook (2007) $7^{th}$ Edition, 3 pages.

Romanova et al., "Study of antioxidant effect of apigenin, luteolin and quercetin by DNA protective method", Neoplasma 48(2) pp. 104-107 (2001).

Salocks et al., FREON®, Technical Support Document: Toxicology Clandestine Drug Labs/Methamphetamine, vol. 1, No. 11, revised Sep. 24, 2003, 14 pages.

Stent and Chelat, downloaded from: www.google.com, Mar. 18, 2013, 3 pgs.

International Search Report for PCT/US2006/027050, dated Apr. 16, 2007, 2 pp.

Kanoh, Soichiro et al., "Mechanisms of Action and Clinical Application of Macrolides as Immunomodulatory Medications," Clin Microbiol Rev., Jul. 2010, 23, 3, pp. 590-615; submission of first page only (1 page).

"Dose—the definition of dose by the Free Dictionary," http://www.thefreedictionary.com/dose,printed Apr. 11, 2017, 1 page.

* cited by examiner

HOLLOW STENT FILLED WITH A THERAPEUTIC AGENT FORMULATION

CROSS-REFERENCE TO RELATED APPLICATION

This application claims the benefit of, and incorporates by reference in its entirety, expressly including any drawings, U.S. Patent Application No. 61/820,155, filed on the 6$^{th}$ of May, 2013.

FIELD OF THE INVENTION

This invention relates to drug compositions to be filled into a structural element of a stent.

BACKGROUND OF THE INVENTION

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies), was coronary by-pass surgery. While effective and evolved to a relatively high degree of safety for such an invasive procedure, by-pass surgery still involves serious potential complications, and in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished and, in addition, PTCA failed to satisfactorily ameliorate another problem, restenosis, the re-clogging of the treated artery.

The next improvement, advanced in the mid-1980s, was use of a stent to hold the vessel walls open after PTCA. This for all intents and purposes put an end to elastic recoil, but did not entirely resolve the issue of restenosis. That is, prior to the introduction of stents, restenosis occurred in 30-50% of patients undergoing PTCA. Stenting reduced this to about 15-30%, much improved but still more than desirable.

In 2003, the drug-eluting stent (DES) was introduced. The drugs initially employed with the DES were cytostatic compounds, compounds that curtailed the proliferation of cells that contributed to restenosis. As a result, restenosis was reduced to about 5-7%, a relatively acceptable figure. Today, the DES is the default industry standard for the treatment of atherosclerosis and is rapidly gaining favor for treatment of stenoses of blood vessels other than coronary arteries such as peripheral angioplasty of the popliteal artery.

The DESs used today have a drug-polymer coating on the exterior surface of the stent. The inclusion of the drug in a polymer matrix secures the drug to the stent surface and allows for sustained delivery over time. One of the limitations of DES is the amount of drug that may be contained in a coating on a device. Another potential drawback is that the polymers used in the coating may contribute to an inflammatory response when the stent is implanted. Depending on the mechanical properties of the coating, it may become damaged during aggressive delivery procedures such as treating calcified lesions, or delivering the DES through a previously deployed stent. Also, the crimping of a DES onto a delivery device, such as the balloon of a catheter, must be done carefully to avoid damaging the coating.

Some alternatives to DES are stents with depots or channels in the structural elements, or struts, of the stent, or stents with some structural elements that are hollow tubes. Therapeutic agents or a composition including therapeutic agents may fill the interior of the hollow tube or a channel or depots.

There is a continuing need for drug formulations that will meet the unique challenges associated with filling the interior of a hollow structural element of a stent or other medical device.

SUMMARY OF THE INVENTION

Various non-limiting embodiments of the present invention are described in the following numbered embodiments:

Embodiment [0001]:

Embodiments of the invention encompass medical devices, where the medical device, includes, but is not limited to including, a device body including, but not limited to, at least one structural element which includes, but is not limited to including, a lumen and at least one opening to access the lumen; and where a composition is within the lumen, the composition including, but is not limited to including, a therapeutic agent, and a metal ion stabilizer.

Embodiment [0002]:

Embodiments of the invention encompass methods including, but not limited to, providing a medical device including but not limited to a device body including but not limited to a structural element or providing a structural element that is to be used in forming at least a part of a medical device body of a medical device where the structural element includes, but is not limited to including, a lumen and at least one opening to access the lumen; and filling the lumen of the structural element with a composition including, but not limited to including, a therapeutic agent, and a metal ion stabilizer.

Embodiment [0003]:

In some embodiments, such as that of embodiment [0002], filling the lumen includes, but is not limited to including, forming a filling composition by executing an operation comprising dissolving, dispersing, or both dissolving and dispersing the therapeutic agent, the metal ion stabilizer, or both the therapeutic agent and the metal ion stabilizer in a solvent, executing an operation comprising placing the filling composition into the lumen, and executing an operation comprising removing the solvent.

Embodiment [0004]:

In some embodiments, such as that of embodiment [0002], filling the lumen includes, but is not limited to including, dissolving, dispersing, or both dissolving and dispersing the therapeutic agent, the metal ion stabilizer, or both the therapeutic agent and the metal ion stabilizer in a solvent, placing the filling composition into the lumen, and removing the solvent.

Embodiment [0005]:

In some embodiments, such as that of embodiment [0002], filling the lumen includes, but is not limited to including, forming a first filling composition by executing an operation comprising dissolving, dispersing, or both dissolving and dispersing the therapeutic agent in a first solvent, executing an operation comprising placing the first filling composition into the lumen, and executing an operation comprising removing the first solvent; and forming a second filling composition by executing an operation comprising dissolving, dispersing, or both dissolving and dispersing the metal ion stabilizer in a second solvent, which may be the same as the first solvent or different from the first solvent, executing an operation comprising placing the second filling composition into the lumen, and executing an operation comprising removing the second solvent.

Embodiment [0006]:
In some embodiments, such as that of embodiment [0002], filling the lumen includes, but is not limited to including, forming a first filling composition by executing an operation comprising dissolving, dispersing, or both dissolving and dispersing the therapeutic agent in a first solvent; forming a second filling composition by executing an operation comprising dissolving, dispersing, or both dissolving and dispersing the metal ion stabilizer in a second solvent, which may be the same as the first solvent or different from the first solvent, executing an operation comprising blending the first and second filling compositions, and executing an operation comprising removing the first and second solvents.

Embodiment [0007]:
In some embodiments, such as that of embodiment [0002], filling the lumen includes, but is not limited to including, forming a first filling composition by executing an operation comprising dissolving, dispersing, or both dissolving and dispersing the therapeutic agent in a first solvent; forming a second filling composition by executing an operation comprising dissolving, dispersing, or both dissolving and dispersing the metal ion stabilizer in a second solvent, which may be the same as the first solvent or different from the first solvent, executing an operation comprising blending the first and second filling compositions, and removing the first and second solvents.

Embodiment [0008]:
In some embodiments, such as any of embodiments [0003]-[0007], removing the solvent or removing at least one of the first and second solvent comprises executing an operation comprising allowing the solvent(s) to evaporate.

Embodiment [0009]:
In some embodiments, such as any of embodiments [0003]-[0007], removing the solvent or removing at least one of the first and second solvents comprises allowing the solvent(s) to evaporate.

Embodiment [0010]:
In some embodiments, such as any of embodiments [0003]-[0007], removing the solvent or removing at least one of the first and second solvents comprises lyophilization.

Embodiment [0011]:
In some embodiments, such as any of embodiments [0003]-[0010], the solvent or at least one of the first and second solvents is a non-polar solvent.

Embodiment [0012]:
In some embodiments, such as any of embodiments [0003]-[0010], the solvent or at least one of the first and second solvents has a solubility parameter of not more than 16 $(MPa)^{1/2}$.

Embodiment [0013]:
In some embodiments, such as any of embodiments [0003]-[0010], the solvent or at least one of the first and second solvents includes, but is not limited to including, a solvent selected from the group consisting of n-hexane, n-heptane, octane, decane, ethyl ether, propyl ether, diisopropyl ether, butyl ether, diisobutyl ketone, and combinations thereof.

Embodiment [0014]:
In some embodiments, such as any of embodiments [0001]-[0013], the medical device is a stent.

Embodiment [0015]:
In some embodiments, such as any of embodiments [0001]-[0014], the device body of the medical device is biostable.

Embodiment [0016]:
In some embodiments, such as that of any of embodiments [0001]-[0015], the device body of the medical device is formed of a biostable metal.

Embodiment [0017]:
In some embodiments, such as that of embodiment [0016], the biostable metal is 316L stainless steel, CoNi, MP35N, CoCr L-605, elgiloy, nitinol or FePtCr.

Embodiment [0018]:
In some embodiments, such as that of embodiment [0017], the biostable metal is MP35N.

Embodiment [0019]:
In some embodiments, such as any of embodiments [0016]-[0018], the walls of the lumen of the at least one structural element of the device body is not electropolished.

Embodiment [0020]:
In some embodiments, such as any of embodiments [0016]-[0018], the degree of electropolishing of the walls of the lumen of the structural element of the medical device is less than the external surface of the device.

Embodiment [0021]:
In some embodiments, such as those of embodiment [0019] or embodiment [0020], the walls of the lumen of the structural element of the medical device may release at least 20% more, at least 50% more, or at least 200% more metal ions than the external surfaces of the structural element of the medical device, but not more than 5000% more metal ions.

Embodiment [0022]:
In some embodiments, such as any of embodiments [0001]-[0021], the metal ion stabilizer, includes, but is not limited to including, a metal chelator.

Embodiment [0023]:
In some embodiments, such as that of embodiment [0022], the metal chelator is selected from the group consisting of ethylene diamine tetraacetic acid (EDTA), calcium disodium EDTA, EDTA with a counterion of potassium, EDTA with a counterion of ammonium, EDTA with a counterion of a quaternary ammonium compound, 2,3-dimereapto-1-propanesulfonic acid, dimercaptosuccinic acid, dimercaprol, desferrioxamine mesylate, alpha lipoic acid, nitrilotriacetate, penicillamine, thiamine tetrahydrofurfiuyl disulfide, deferiprone, deferasirox, kojic acid, bisphosphonates, 3,4-hydroxypyridinecarboxylic acids, including but not limited to 3-hydroxy-4-pyridinecarboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid, and combinations thereof.

Embodiment [0024]:
In some embodiments, such as that of embodiment [0022], the metal chelator is selected from the group consisting of sodium ascorbate, desferrioxamine, malic acid, citric acid, succinic acid, sodium, calcium, and magnesium salts of malic acid, citric acid, and succinic acid, feralex-G, clioquinol, curcumin, epigallocatechin, 3-hydroxy-4-pyridinone derivatives, including, but not limited to, 3-hydroxy-4-pyridinecarboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid, and combinations thereof.

Embodiment [0025]:

In some embodiments, such as any of embodiments [0001]-[0024], the metal ion stabilizer, includes, but is not limited to including, a precipitation agent.

Embodiment [0026]:

In some embodiments, such as that of embodiment [0025], the precipitation agent is selected from the group consisting of stearic acid, lauric acid, capric acid, and caprylic acid, and sodium, calcium, and magnesium salts thereof.

Embodiment [0027]:

In some embodiments, such as any of embodiments [0001]-[0026], the combination of the therapeutic agent and the metal ion stabilizer comprise at least 50 wt % of the composition filling the lumen, and not more than 100 wt %.

Embodiment [0028]:

In some embodiments, such as that of embodiment [0027], the combination of the therapeutic agent and the metal ion stabilizer comprise at least 70 wt % of the composition, and not more than 100 wt %.

Embodiment [0029]:

In some embodiments, such as that of embodiment [0028], the combination of the therapeutic agent and the metal ion stabilizer comprise at least 90 wt % of the composition, and not more than 100 wt %.

Embodiment [0030]:

In some embodiments, such as any of embodiments [0001]-[0029], the weight percent of the metal ion stabilizer relative to the therapeutic agent is in the range of 0.01 to 25 wt %.

Embodiment [0031]:

In some embodiments, such as that of embodiment [0030], the weight percent of the metal ion stabilizer relative to the therapeutic agent is in the range of 0.1 to 10 wt %.

Embodiment [0032]:

In some embodiments, such as that of embodiment [0031], the weight percent of the metal ion stabilizer relative to the therapeutic agent is in the range of 0.2 to 8%.

Embodiment [0033]:

Embodiments of the invention encompass stents, including, but not limited to including, a plurality of interconnected structural elements comprising a metallic material, wherein at least some of the structural elements are annular and comprise an interior lumen; and a therapeutic agent and an additive, optionally with in combination with other substances, disposed within the interior lumen of at least some of the structural elements comprising an interior lumen; wherein an inner surface of the annular structural elements is susceptible to release of metal ions which are capable of degrading the therapeutic agent; and wherein the additive is for protecting the therapeutic agent from degradation by the metal ions by rendering the metal ions unable to interact with the therapeutic agent.

Embodiment [0034]:

In some embodiments, such as that of embodiment [0033], the additive is a compound that binds to the metal ions, rendering them unable to interact with the therapeutic agent.

Embodiment [0035]:

In some embodiments, such as that of embodiment [0034], the compound is selected from the group consisting of chelating agents, cryptands, ligands, multidentate ligands, and combinations thereof.

Embodiment [0036]:

In some embodiments, such as that of embodiment [0035], the compound is selected from the group consisting of ethylene diamine tetraacetic acid (EDTA), calcium disodium EDTA, EDTA with a counterion of potassium, EDTA with a counterion of ammonium, EDTA with a counterion of a quaternary ammonium compound, 2,3-dimereapto-1-propanesulfonic acid, dimercaptosuccinic acid, dimercaprol, desferrioxamine mesylate, alpha lipoic acid, nitrilotriacetate, penicillamine, thiamine tetrahydrofurfiuyl disulfide, deferiprone, deferasirox, kojic acid, bisphosphonates, 3,4-hydroxypyridinecarboxylic acids, including but not limited to 3-hydroxy-4-pyridinecarboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid, and combinations thereof.

Embodiment [0037]:

In some embodiments, such as that of embodiment [0035], the compound is selected from the group consisting of sodium ascorbate, desferrioxamine, malic acid, citric acid, succinic acid, sodium, calcium, and magnesium salts of malic acid, citric acid, and succinic acid, feralex-G, clioquinol, curcumin, epigallocatechin, 3-hydroxy-4-pyridinone derivatives, including, but not limited to, 3-hydroxy-4-pyridinecarboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid, and combinations thereof.

Embodiment [0038]:

In some embodiments, such as that of embodiment [0033], the additive is a compound that forms an insoluble metal salt with the metal ions to prevent the metal ion from interacting with the therapeutic agent.

Embodiment [0039]:

In some embodiments, such as that of embodiment [0038], the compound is selected from the group consisting of stearic acid, lauric acid, capric acid, and caprylic acid, and sodium, calcium, and magnesium salts thereof.

Embodiment [0040]:

In some embodiments, such as any of embodiments [0033]-[0039], less than 5 weight % of the therapeutic agent is degraded at the end of a shelf life of the therapeutic agent.

Embodiment [0041]:

In some embodiments, such as any of embodiments [0033]-[0039], the therapeutic agents is degraded by not more than 5 weight % at the end of the self-life of the stent, and wherein the shelf-life of the stent is at least 6 months, at least 9 months, at least 12 months, at least 18 months, or at least 24 months.

Embodiment [0042]:

In some embodiments, such as any of embodiments [0033]-[0041], the metallic material is biostable.

Embodiment [0043]:

In some embodiments, such as any of embodiments [0033]-[0042], the inner surface of the annular structural elements is more susceptible to release of metal ions than an outer surface of the annular structural elements due to a passivation layer on the outer surface.

Embodiment [0044]:

In some embodiments, such as any of embodiments [0033]-[0043], the therapeutic agent is a member of the macrolide lactone family and the therapeutic agent contains a triene moiety.

Embodiment [0045]:

Embodiments of the invention encompass a hollow stent formed from a biostable metal, where a hollow stent is a stent including, but not limited to, at least one strut comprising a lumen and at least one opening to access the lumen; and where the lumen of the strut at least partially filled with a metal ion stabilizer and a therapeutic agent which is a member of the macrolide lactone family and the therapeutic agent contains a triene moiety.

Embodiment [0046]:

In some embodiments, such as that of any of embodiment [0045], the metal ion stabilizer is or at least comprises calcium disodium EDTA.

DETAILED DESCRIPTION

Figure 1B:
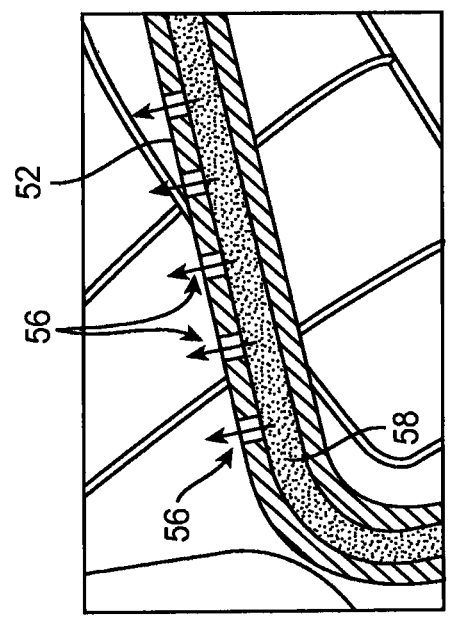
FIG. 1B depicts a close-up of a hollow strut of an exemplary embodiment of a stent.

Use of the singular herein (including the claims), includes the plural and vice versa unless expressly stated to be otherwise. That is, "a" and "the" refer to one or more of whatever the word modifies. For example, "a stent" may refer to one stent, two stents, etc. Likewise, "the polymer" may mean one polymer or a plurality of polymers. By the same token, words such as, without limitation, "stents" and "polymers" would refer to one stent or polymer as well as to a plurality of stents or polymers unless it is expressly stated or obvious from the context that such is not intended.

As used herein, words of approximation such as, without limitation, "about," "substantially," "essentially," and "approximately" mean that the word or phrase modified by the term need not be exactly that which is written but may vary from that written description to some extent. The extent to which the description may vary from the literal meaning of what is written, that is the absolute or perfect form, will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by ±15%, unless expressly stated otherwise.

As used herein, any ranges presented are inclusive of the end-points. For example, "a weight % between 1% and 10%" or "a weight % from 1% to 10%" includes 1 weight % and 10 weight %, as well as any weight % in between, including fractions such as, but not limited to, 2.5%.

As used herein, a "polymer" refers to a molecule comprised of, either actually or conceptually, repeating "constitutional units." The constitutional units may derive from the reaction of monomers. As a non-limiting example, ethylene ($CH_2$=$CH_2$) is a monomer that can be polymerized to form polyethylene, $CH_3CH_2(CH_2CH_2)_nCH_2CH_3$, wherein n represents an integer, and the constitutional unit is —$CH_2CH_2$—, ethylene having lost the double bond as the result of the polymerization reaction. A polymer may be derived from the polymerization of several different monomers and therefore may comprise several different constitutional units. Such polymers are referred to as "copolymers." The constitutional units themselves can be the product of the reactions of other compounds. As used herein, a molecule of more than 20 constitutional units is a polymer. Those skilled in the art, given a particular polymer, will readily recognize the constitutional units of that polymer and will equally readily recognize the structure of the monomer from which the constitutional units derive. A polymer may be a linear chain, a branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

An "oligomer" is a molecule comprised of, either actually, or conceptually, repeating constitutional units, but where the number of constitutional units is too small to be considered to be a polymer. As used herein, an oligomer is a molecule of 20 or fewer constitutional units.

As used herein, "biocompatible" refers to a material that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms bioresorbable, biodegradable, bioabsorbable, bioerodable, biosoluble, absorbable, and resorbable, as well as degradable, erodable, and dissolvable, are used interchangeably, and refer to materials that are capable of being completely eroded, degraded, either biodegraded and/or chemically degraded, and/or absorbed when exposed to bodily fluids, such as blood, and can be gradually resorbed, absorbed and/or eliminated by the body.

Conversely, a "biostable" material refers to a material that is not biodegradable, or which biodegrades over a long time period, such as 10 years or more than 10 years, under the conditions of use. A device made from a biostable material will remain at an implant site (unless it is moved) and retains its physical form for an extended period of time that typically encompasses the lifetime of the patient, or the remaining lifetime of the patient.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed.

One form of implantable medical device is a "stent." A stent refers generally to any device used to hold tissue in place in a patient's body. Stents may be typically tubular shaped devices. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease such as, without limitation, atherosclerosis, carotid artery disease, peripheral arterial disease, restenosis and vulnerable plaque.

Other medical devices may be referred to as an insertable medical device, that is any type of appliance that is totally or partly introduced, surgically or medically, into a patient's body or by medical intervention into a natural orifice, but the device does not remain in the patient's body after the procedure.

A "lumen" as defined by Webster's Medical Dictionary is the channel within a tube such as a blood vessel, or the interior of a hollow organ such as the intestine. The term lumen is usually an anatomical term. As used herein, the term "lumen" may be broader, and may not only refer to the anatomy of an animal, but may also refer to the channel inside a tube or a tubular shaped object.

As used herein, a "hole" is an opening or a channel in a material created by any one or more of a combination of etching, laser machining, mechanical machining, drilling, and conventional processes known by persons of ordinary skill in the art. The location of holes may be predetermined.

As used herein, a "pore" is an opening or channel in a material that naturally results from the properties of the material. The location of pores may not be pre-determined.

As used herein, the terms "pores" and "holes" will be used interchangeably unless expressly stated otherwise.

As used herein, a material that is described as a layer or a film (e.g., a coating) "disposed over" an indicated substrate refers to a coating of the material deposited directly or indirectly over at least a portion of the surface of the substrate. "Directly deposited" means that the coating is applied directly to the surface of the substrate. "Indirectly deposited" means that the coating is applied to an intervening layer that has been deposited directly or indirectly over the substrate. The terms "layer", and "coating layer" will be used interchangeably and refer to a layer or film as described in this paragraph. A coating may be one layer or more than one layer. Each layer may be formed by one or multiple applications of coating material. In general, a 'coating layer' of a given material is a region of that material whose thickness is small compared to both its length and width (for example, the length and width dimensions may both be at least 5, 10, 20, 50, 100 or more times the thickness dimension in some embodiments). A coating and a coating layer are supported by the substrate. A coating layer may be discontinuous. Unless the context clearly indicates otherwise, a reference to a coating, layer, or coating layer refers to a layer of material that covers all, or substantially all, of the surface, whether deposited directly or indirectly.

As used herein, a "therapeutic agent" refers to any substance that, when administered in a therapeutically effective amount to a patient suffering from a disease or condition, has a therapeutic beneficial effect on the health and well-being of the patient (an animal, including a human). A therapeutic beneficial effect on the health and well-being of a patient includes, but is not limited to: (1) curing the disease or condition; (2) slowing the progress of the disease or condition; (3) causing the disease or condition to retrogress; or, (4) alleviating one or more symptoms of the disease or condition.

As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent" also refers to pharmaceutically acceptable, pharmacologically active derivatives of those therapeutic agents specifically mentioned herein, including, but not limited to, salts, esters, amides, and the like. Substances useful for diagnostics are also encompassed by the term "therapeutic agent" as used herein.

As used herein, the terms "therapeutic agent," "drug," "bioactive agent", "biologically active agent," "biological agent," and "active ingredient," will be used interchangeably.

A "pharmaceutical formulation" may be a therapeutic agent in combination with a pharmaceutical excipient. A pharmaceutical formulation may be a solid, semi-solid, a gel, a liquid, a suspension, a powder, or another physical form.

As used herein, an "excipient" may be a substance that is combined with a therapeutic agent to form a final dosage form. Excipients are non-toxic, and are typically inert, that is the excipient itself is not a therapeutic agent. Excipients typically perform a function such as acting as a binder for the therapeutic agent, a carrier or a diluent for the therapeutic agent, a permeation enhancer, or an antioxidant or stabilizer for the therapeutic agent. In some cases vitamins, minerals, or both, which may have therapeutic uses themselves, may also be an excipient. One of skill in the art can readily determine if a vitamin or mineral or other substance is being used as an excipient in a pharmaceutical formulation, if the vitamin or mineral is a therapeutic agent in the pharmaceutical formulation, or if the vitamin or mineral serves a dual purpose. Unlike a solvent which is removed from the final dosage form, an excipient is not removed, but remains part of the final dosage form.

A chelate is typically described as a compound in which a metal ion is attached by coordinate bonds to at least two non-metal ions. The compound is often in the form of a ring. As used herein a "chelator" will be broadly defined as a compound which binds a metal ion such that it cannot interact with a therapeutic agent. Typically, these types of compounds are referred to as chelating agents, chelators, cryptands, ligands, and multidentate ligands.

As used herein a "precipitation agent" is a compound that forms an insoluble metal salt with any metal ions to prevent the metal ion from interacting with other compounds present, such as a drug.

As used herein, the term "metal ion stabilizer" will be used to refer to a metal ion chelator, a chelating agent, a cryptand, a ligand, a multidentate ligand, a precipitation agent, or a combination thereof.

As used herein, a "solvent" can be a substance capable of dissolving, partially dissolving, dispersing, or suspending one or more substances to form a uniform dispersion and/or solution, with or without agitation, at a selected temperature and pressure, and which is not an excipient. The substance may be a liquid, a gas, or a supercritical fluid. A solvent herein may be a blend of two or more such substances. As used herein, a substance used as an excipient in a pharmaceutical formulation is not a solvent even if it is capable of dissolving, partially dissolving, dispersing, or suspending one or more substances to form a uniform dispersion and/or solution. As used herein, a solvent may be used as a processing aid in forming a pharmaceutical formulation, but is removed, or substantially removed, during processing and does not form part of the final pharmaceutical formulation (except for incidental residual solvent).

Aspects of the present invention are directed to medical devices, and especially stents, in which at least some of the structural elements, which may be struts, have a lumen. In other words, the struts or structural elements can be, for example, essentially hollow cylinders or tubes. The following description will refer to stents as an example of a medical device, but embodiments of the invention are not so limited.

As noted previously, a stent can be any device used to hold tissue in place in a patient's body. A stent can be a tubular shaped device formed of a scaffolding of a plurality of interconnecting structural elements, or struts. Other variations of stents include coiled or helical stents, and fibers or filaments, which may be braided or woven, forming the structural elements of the stent. It is the scaffolding that provides support or outward radial force to support tissue, such as a vessel wall, when implanted. The pattern of the scaffolding, or stent pattern, can be designed so that the stent can be radially compressed (crimped) and radially expanded (to allow deployment). The cross-section of the stent and the structural elements forming the stent is not limited to a circle, but may be elliptical or some other cross-section. Typical stent dimensions for an expanded coronary stent can be 2 to 5 mm in diameter, and 6 to 50 mm in length. Typical dimensions for an expanded peripheral stent are 3 to 8 mm in diameter, 8 mm to 200 mm in length, and about 60 microns to 250 microns in strut thickness. Aspects of the present invention are directed to devices, such as stents, in which at least some of the structural elements, which may be struts, have a lumen. In other words, the struts can be, for example, are hollow cylinders, or are essentially hollow cylinders. In some embodiments, the stent includes structural elements in which the lumen extends for less than the entire length of the structural element, or the structural element is only hollow for part of its length. The lumen in a structural element may be discontinuous.

Figure 1A:
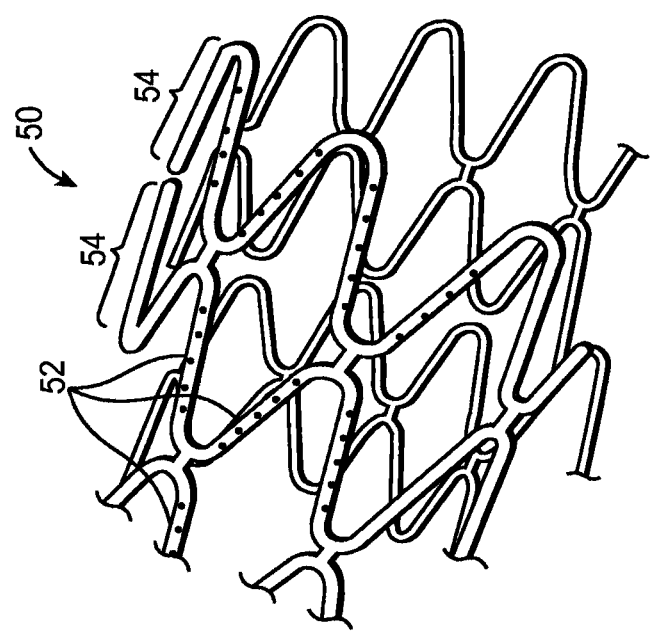
FIG. 1A depicts an exemplary and non-limiting embodiment of a stent with hollow struts.

Referring now in more detail to the exemplary drawings for purposes of illustrating embodiments of the invention, wherein like reference numerals designate corresponding or like elements among the several views, there is shown in FIG. 1A an exemplary stent 50 comprising a plurality of interconnected stent struts 52 configured to move relative to each other. The stent struts 52 can be, for example, arranged in a sinusoidal or serpentine pattern. The stent struts 52 can form a plurality of circumferential rings 54 that may be arranged axially to form a tubular scaffold configured to support biological tissue after implantation of the stent. The rings may be connected by as few as one linking strut per ring, but two, three, or more may be present, or many more as depicted in FIG. 1A. Surfaces of the tubular scaffold that face radially inward are referred to collectively as the luminal surface of the stent. Surfaces of the tubular scaffold that face radially outward are referred to collectively as the abluminal surface of the stent. The abluminal surface is a tissue contacting surface for a stent used in a blood vessel. In some embodiments, the structural elements forming the scaffold have sidewall surfaces that connect the abluminal and luminal surfaces. The "outer surface" of a stent may be any surface that would be in contact with tissue or blood when implanted in a patient and therefore includes abluminal and luminal surfaces and if present, sidewall surfaces, and does not include the interior surfaces of the lumen of any structural elements comprising an interior lumen. In other words, if the device includes one or more structural elements including an internal lumen, the outer surface is the surface in contact with blood or tissue when implanted assuming that all side openings to access any internal lumens of the structural elements are plugged or closed. The pattern shown in FIG. 1A is an exemplary embodiment, and the embodiments of the invention are not limited to what has been illustrated as other stent patterns are easily applicable. Specifically, a stent which is a helix and/or coil is an alternative configuration. The stent may be comprised of individual ring sections, or made of one length of wire or tubing.

The rings 54 can be configured to be collapsed or crimped to a smaller diameter, thereby allowing the stent to be secured onto a balloon or other device for delivering the stent to the desired implantation site within a patent. The rings 54 can be also configured to expand when inside the patient. The rings 54 can be expanded by inflation of a balloon on which the stent has been crimped, or alternatively, the rings can self-expand like a spring upon removal of an outer sheath, or other restraint.

Each strut 52 and ring 54 may be, for example, made of a continuous tube of material, a cross section of which is shown in FIG. 1B. The struts 52 formed from the continuous tube are referred to herein as "strut tubes." These strut tubes are exemplary, but not limiting, structural elements of a stent. Although the exemplary stent is shown with a struts have a circular or essentially circular cross-section, the cross-section of struts or structural elements is not limited to these, and may be elliptical, polygonal, rectangular, etc. The tube stock used to make the struts can be made from an extrusion process or other processes known in the art for making tube stock. Although the precise dimensions of the tube stock may vary depending upon the intended use of the stent, suitable tube stock diameters and wall thicknesses for coronary use may be between 40 and 200 microns and 10 to 80 microns, respectively. The tube stock is uniform or essentially uniform in diameter and cross-section over its length, but in some embodiments, the diameter and internal cross-section may vary or fluctuate over the length of the tube. To make the stent, the tube stock may be bent into the serpentine pattern, and then wrapped around circumferentially to form the ring. Thus, bending may result in a change both the shape of the cross section as well as the internal cross-sectional area. A plurality of the rings can be made from a single, continuous tube. Alternatively, each ring can be made from its tube, and the rings can be connected by welding or bonding the tubes together or by attaching links to adjacent rings. In either case, there can be openings at one or both ends of the tube providing access to the lumen. In some embodiments, one opening at the end of the tube may be sealed, or plugged. In other embodiments, the ends of the tubes are joined together, leaving no openings at tube ends.

Figure 2:
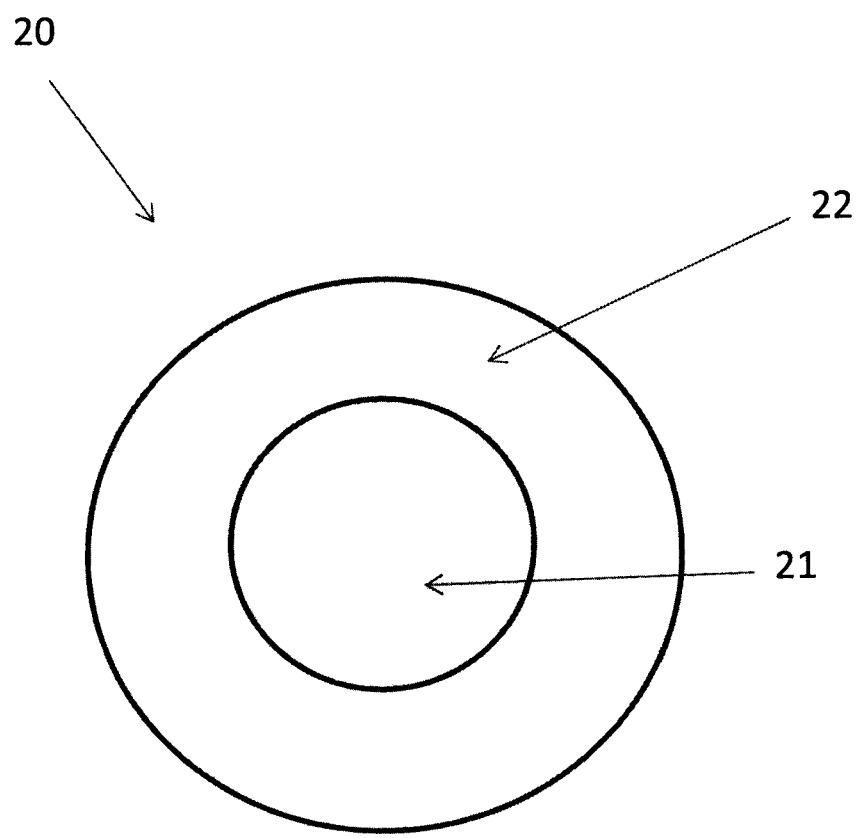
FIG. 2 depicts a cross-section of a co-extruded wire.

In other embodiments, the stock for forming structural elements of the stent is a coextruded wire. An example of a cross-section of a co-extruded wire 20 is depicted in FIG. 2 where there is a core (21) and an outer shell (22) of the wire. The wire may be formed into a pattern, such as but not limited to, the crests of a sinusoid (as an example of a stent pattern). Holes may be drilled into a surface, such as without limitation, the surface that will be the abluminal surface. These holes will become the side openings discussed below. The wire may be wound onto a mandrel in a pattern such as but not limited to a spiral, and links may be formed between rings. One means of forming the links is laser welding. Finally, the stent may be exposed to an etching gas which selectively removes the sacrificial core of the co-extruded wire by sublimation. Thus, the stent formed has a lumen in at least some of the struts.

In the discussion that follows a reference to a strut tube or a structural element for use in a method or use with an apparatus or the like is not so limited and embodiments of the invention also encompass the use of a stent instead. Likewise, a reference to a stent in the description is not so limited and embodiments of the invention also encompass the use of the strut tubes or structural elements instead of the stent. As an example, and without limitation, the disclosure of immersing a structural element having a lumen into a material encompasses both immersion of an individual ring or strut tube into the material as well as the immersion of an entire stent having a strut tube.

A plurality of holes and/or pores, referred to hereinafter as side openings 56 (FIG. 1B), exist in the strut tubes. In one aspect of the invention, the side openings may be pores and may not include holes formed at predetermined locations. In another aspect of the invention, the side openings may be holes formed at pre-determined locations and not include any pores. In still another aspect, the side openings may be a combination of pores and holes formed at pre-determined locations. Each side opening 56 accesses the lumen of the strut tube 52 so that any composition 58 carried inside the lumen can escape out of the openings after the stent is implanted (as depicted by arrows in FIG. 1B). The composition may include a therapeutic agent. One or more of the side openings are in fluid communication with each other through the internal lumen. Although the side openings are illustrated as essentially circular in cross-section, the cross-section is not so limited and the openings may be of any shape or any combination of shapes, such as, without limitation, elliptical, rectangular, circular, or polygonal. The side openings extend from the internal surface or luminal surface of the strut tube to the exterior surface of the strut tube. The side openings may be in the abluminal, luminal, and/or sidewall surfaces of the strut. The side opening may be in the form of a channel or slit with a uniform or substantially uniform cross-section, or the cross-section may vary. The aspect ratio of the opening may be 1, from 1 to 10, or in some cases greater than 10. The aspect ratio is the width to height of an object, or more generally, the ratio of longest dimension and the shortest dimension of an object. In this case the aspect ratio is the longest dimension and the shortest dimension of the opening.

The side openings may be of a diameter that is significantly smaller than that of the openings at the ends of the tube if end openings are present. In some embodiments, the size of an individual side opening, as determined by the area of the side opening on the internal surface of the tube is not more than 50% of the cross-sectional area of the opening at the end of the tube. As used herein "not more than 50% of the cross-sectional area of the opening at the end of the tube" means the smaller of the areas if the two end openings are present and do not have the same cross-sectional opening area. In an aspect of the present invention, this ratio is not more than 25%, and in still another aspect of the invention, not more than 10%. In another aspect of the invention, this ratio is not more than 5%. The side openings may be distributed along the length of each structural element. There may be about 4 to 144 side openings per ring. In other embodiments there may be fewer than 4 side openings per ring, and in still other embodiments, there may be more than 144 openings per ring. The distance between the side openings may be uniform or non-uniform. In some embodiments, the side openings are distributed along the length of at least one structural element, the separation between the openings being approximately uniform (not more than 25% difference between the smallest distance and the largest distance between openings).

Polishing and cleaning can be performed after the side openings 56 are formed in order to remove debris, burs and/or sharp edges. The side openings 56 can be made before or after the stock tube is formed into the struts and rings of the stent. In some embodiments, initially, the stock tubes are hollow and contain no material. In other embodiments, the stock is a coextruded wire.

After completion of the manufacturing process, the strut tubes 52 contain a composition 58 which may include therapeutic agent and/or other substances, some of which it may be desired to be released out from the stent after implantation. The composition can be filled in before or after the stock tube is formed into the struts and rings of the stent. The composition can be filled in before or after the side openings 56 are formed. Processes for tube bending, creating the side openings, polishing and cleaning may generate heat, involve the application of heat to the tube, or use corrosive chemicals. Therefore, when the composition to be filled into the tube is heat sensitive, prone to degradation when exposed to heat, or susceptible to the chemicals used, it is preferred to load the tube with the composition after the tube has been formed into the struts and rings of the stent, after the side openings are formed, and after any polishing. If co-extruded wire is used at least removal of the core material must be completed before filling the strut tubes.

The tubes, or the structural elements, used to form a stent are generally made from, but not required to be made from, a biocompatible metal or metal alloy. Exemplary metals and metal alloys include, without limitation, cobalt-chromium alloys (e.g., ELGILOY™ Haynes alloy 25™, L-605) stainless steel (316L), "MP35N," "MP20N," ELASTINITE™ (nitinol), platinum modified stainless steel, FePtCr, tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Examples of co-extruded wires where the first and second materials are the outer tube and core material, respectively, include MP35N/aluminum, MP35N/magnesium, MP35N/zinc, L-605/iron, and nitinol/tin. In some embodiments, the structural elements forming the device body, or in other words, the device body, is made from biostable materials, such as a biostable metal, a biostable polymer, or a combination thereof. In some embodiments, the device body or strut tubes are made completely of biostable materials such as biostable metals and are not made of biodegradable materials such as biodegradable polymers or metals. In other embodiments, the structural elements forming the device body, or in other words, the device body, are made from biostable materials, such as a biostable metal, a biostable polymer, or a combination thereof. The device body may be made from other materials such as ceramics, and/or glass. Any of the above materials may be used in combination. In other embodiments, the structural elements forming the device body, or in other words, the device body, are made from biodegradable materials, such as and without limitation biodegradable polymers, biodegradable metals, biodegradable glasses, biodegradable ceramics, or any combination thereof.

As noted above, the lumen of the strut tube is intended to be filled, or loaded, with one or more substances, such as a pharmaceutical composition, hereinafter a "composition." Thus the substance filling or loaded into the strut tube lumen and which are intended to remain there until the stent is implanted may be referred to as a composition, and may include a therapeutic agent, and/or other substances.

Aspects of the present invention are directed to compositions for use in medical devices, such as stents, having hollow struts or structural elements with a lumen (a.k.a. "a hollow stent"), and medical devices filled (partially, completely, or substantially completely (at least 90% of the volume)) with the compositions. As used herein, "filling" and "loading" the lumen of a structural element of a device, such as a stent, refers to at least partially filling the lumen, and encompasses partially filing, complete filling, and substantially complete filling of the lumen. Medical devices, such as stents, with hollow struts that are accessible via at least one opening to the exterior have the potential for more ion release due to several causes. One difference between hollow versus conventional metallic stents is the increased surface area of exposed metal that leads to more metal ion release.

Metallic stents may be electropolished and their surfaces are highly characterized. Electropolishing, also known as electrochemical polishing or electrolytic polishing (especially in the metallography field), is an electrochemical process that removes material from a metallic workpiece. It is used to polish, passivate, and deburr metal parts. Passivation, refers to a material becoming "passive," that is, being less affected by environmental factors such as air or water. For the alloys used to make stents, electropolishing enriches the surface in the most corrosion resistant oxide of the alloy composition which is often chromium oxide. This passive oxide layer, which will form spontaneously on many alloys, serves as a corrosion resistant shield for the underlying alloy. As a technique, passivating is typically a chemical treatment to generate a light coat of material such as metal oxide to create a barrier against corrosion. Electropolishing makes a metal surface less reactive, will produce a thick and uniform layer of oxide with some alloys, and render the surface less susceptible to release of metal ions.

The outside surface of the stent of the present invention may be electropolished and have the characteristics of an electropolished surface described herein. However, electropolishing the inside surface of the hollow structural elements is much more difficult than the outside. At least a portion of or all of the interior walls of the lumen of a structural element (interior lumen walls), such as a strut of a stent, may not be electropolished. A more "raw" surface inside the struts will be more reactive and may release more metallic ions than an electropolished surface. In addition, the interior walls of the lumen of a structural element, such as a strut of a stent, may not be electropolished, or may be electropolished less than an outer surface (exterior surface) of the structural element of the device.

Since electro-polishing increases the inertness of the metal, the lumen of a structural element (interior walls) will be more likely than an electropolished surface to release metal ions. In addition, if the device is formed using a co-extruded wire with a core of a sacrificial metal, the sacrificial metal may not be completely removed, thus providing the potential for further metal ion generation. In some embodiments, the interior or inner walls of the lumen of the structural element of the medical device are less electropolished than the exterior surfaces of the structural element and as a result may release at least 20% more, at least 50% more, or at least 200% more metal ions than the exterior surfaces of the structural element of the medical device, but not more than 5000% more metal ions.

Some therapeutic agents, and potentially some excipients, may interact with metal ions. Regulatory agencies such as the United States Food and Drug Administration consider a product containing a therapeutic agent to have undergone a significant change if 5% or more of the therapeutic agent is degraded during manufacturing process or shelf-life. Consequently, this level of degradation can represent expiry of the product. Thus, filling of a lumen of a hollow stent with a composition may impact the stability of the therapeutic agent, the composition including the therapeutic agent, or both due to the potential interactions with metal ions. A category of therapeutic agents that are particularly sensitive are those which are in the macrolide lactone family and which contain a triene moiety. Some therapeutic agents, such as those in the macrolide lactone family and which contain a triene moiety, are subject to metal ion induced oxidation and metal ion catalyzed degradation processes including hydrolysis and oxidation/reduction reactions. Thus, embodiments of the present invention encompass compositions for filling the lumen of a structural element of a medical device, such as the lumen of a hollow strut of a stent, and medical devices with a structural element containing a lumen having the lumen filled with the compositions. The compositions include a therapeutic agent and a metal ion stabilizer, such as but not limited to, a metal chelator, chelating agent, a cryptand, a ligand, a multidentate ligand, a precipitation agent, or a combination thereof.

Therapeutic agents, such as but not limited to those described herein, may be used individually or in any combination in any proportion in the compositions described herein. In preferred embodiments, the therapeutic agent of the composition is a member of the macrolide lactone family and the therapeutic agent contains a triene moiety. Examples of such therapeutic agents include, but are not limited to: rapamycin (sirolimus), everolimus (40-O-(2-hydroxy) ethyl-rapamycin), biolimus A9 (Biosensors International, Singapore), umirolimus, ridaforolimus (a.k.a. AP23573, Ariad Pharmaceuticals; formerly known as deforolimus), tacrolimus, temsirolimus, pimecrolimus, novolimus, merilimus, myolimus, zotarolimus (a.k.a. ABT-578, Abbott Laboratories), 40-O-(3-hydroxypropyl)rapamycin, 40-O-[2-(2-hydroxy)ethoxy]ethyl-rapamycin, 40-O-tetrazolylrapamycin, and 40-epi-(N1-tetrazolyl)-rapamycin. Therapeutic agents also included in the preferred embodiments are those compounds with a structure of rapamycin but with a substituent at the carbon corresponding to the 42 or 40 carbon of rapamycin as shown below:

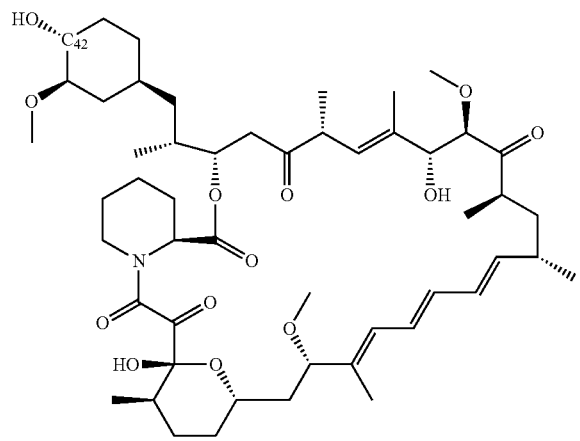

Rapamycin with the 42 carbon labeled.

The carbon labeled $C_{42}$ in the above figure is sometimes labeled $C_{40}$ depending upon the numbering scheme used. Thus, instead of "OH" at $C_{42}$ as shown above in rapamycin, another moiety would be substituted for the "OH."

Compositions described herein may include other therapeutic agents, individual therapeutic agents or a combination of these, in addition to or instead of the ones described above.

Metal stabilizers, such as but not limited to those described herein, may be used individually or in any combination in any proportion in the compositions described herein.

Examples of metal chelators for D-block metal ions (such as but not limited to iron, chromium, nickel, and cobalt) that may be used in the embodiments of the invention described herein, include, but are not limited to: ethylene diamine tetraacetic acid (EDTA); calcium disodium EDTA; EDTA with a more hydrophobic counterion to render it organic soluble, where such counterions include, but are not limited to, potassium, ammonium, and quaternary ammonium compounds; 2,3-dimereapto-1-propanesulfonic acid (DMPS); dimercaptosuccinic acid (DMSA); dimercaprol; desferrioxamine mesylate; alpha lipoic acid (ALA); nitrilotriacetate; penicillamine; thiamine tetrahydrofurfuryl disulfide (TTFD); deferiprone; deferasirox; kojic acid and kojic acid derivatives, such as but not limited to 6-[5-hydroxy-2-hydroxymethyl-pyran-4-one]-5-hydroxy-2-hydroxymethyl-pyran-4-one; bisphosphonates, such as but not limited to etidronic acid, pamidronate, alendronate and 1-phenyl-1-hydroxymethylene bisphosphonate; and 3,4-hydroxypyridinecarboxylic acids, such as but not limited to 3-hydroxy-4-pyridine-carboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid. With respect to metal chelators for D-block metal ions, a preferred metal chelator is calcium disodium EDTA. Calcium disodium EDTA is currently used clinically in chelation therapy to treat excess of iron in the body.

Examples of biocompatible metal chelating agents for aluminum that may be used in the embodiments of the invention described herein, include, but are not limited to: sodium ascorbate (vitamin C); desferrioxamine; malic acid (sodium, calcium or magnesium salt); citric acid (sodium, calcium or magnesium salt); succinic acid (sodium, calcium or magnesium salt); feralex-G; clioquinol; curcumin; epigallocatechin; and 3-hydroxy-4-pyridinone derivatives, such as but not limited to 3-hydroxy-4-pyridinecarboxylic acid, 4-hydroxy-3-pyridinecarboxylic acid, 1,6-Dimethyl-4-hydroxy-3-pyridinecarboxylic acid and 4-hydroxy-2-methyl-3-pyridinecarboxylic acid.

Precipitation agents may be used in the embodiments of the invention described herein. Aluminum ion (III) reacts with stearate and forms insoluble tri-aluminum stearate. Other hydrophobic fatty acids such as laurate, caprate, and caprylate will work similarly. Examples of precipitation agents for aluminum include, but are not limited to: stearic acid (a fatty acid); sodium stearate; laurate; sodium laurate; caprate; sodium caprate; caprylate; sodium caprylate; and other biocompatible and soluble salts of these.

The use of anti-oxidants such as butylated hydroxytoluene (BHT) in the formulation will not limit or prevent the impact of the metal ions on the degradation of the therapeutic agent in the composition. Thus, any stabilizers can be specifically selected to protect the therapeutic agent from degradation resulting from exposure to metal ions.

In some embodiments, the composition includes a therapeutic agent, and an ion stabilizer, such as a metal chelator, a precipitation agent, or both a metal chelator and a precipitation agent. In some embodiments, the composition consists essentially of a therapeutic agent, and a metal ion stabilizer, where consists essentially of means at least 98 weight percent. In some embodiments, the composition consists of a therapeutic agent, and a metal ion stabilizer. In some embodiments, the composition consists of therapeutic agent (in other words "pure drug"). In some embodiments, the composition includes a therapeutic agent and a metal ion stabilizer, and the sum of the weight percent (wt %) of the therapeutic agent and the metal ion stabilizer is at least 50 wt % of the composition and not more than 100 wt % of the composition, while in other embodiments the sum is at least 60 wt %, at least 70 wt %, at least 80 wt %, at least 90 wt %, at least 95 wt %, or at least 98 wt %, and not more than 100 wt % of the composition.

In some embodiments, the composition includes an excipient in addition to the therapeutic agent and the metal ion stabilizer. In some embodiments, the composition is free of, or essentially free of, polymers. In some embodiments, the composition is free of, or essentially free of, oligomers. In some embodiments, the composition is free of, or essentially free of, both polymers and oligomers.

In some embodiments, the weight percent of the metal ion stabilizer relative to the therapeutic agent ((weight of metal ion stabilizer/weight of therapeutic agent)×100%) is in the range of 0.01 to 25%, preferably in the range of 0.1 to 10%, and more preferably in the range of 0.2 to 8%.

In some embodiments, the composition includes a sufficient amount of a metal ion stabilizer such that there is at least 0.025 µg metal ion stabilizer/cm$^2$ of interior surface of the lumen and not more than 25 µg metal ion stabilizer/cm$^2$ of interior surface of the lumen, preferably at least 0.1 µg metal ion stabilizer/cm$^2$ of interior surface of the lumen and not more than 15 µg metal ion stabilizer/cm$^2$ of interior surface of the lumen, and even more preferably at least 0.25 µg metal ion stabilizer/cm$^2$ of interior surface of the lumen and not more than 10 µg metal ion stabilizer/cm$^2$ of interior surface of the lumen. The "interior surface of the lumen" may refer to all of the interior surfaces of the medical device, or all the interior surface of the lumen only for those lumens which will be filled with a composition including a therapeutic agent and a metal ion stabilizer.

In some embodiments, the composition includes a therapeutic agent and a sufficient amount of a metal ion stabilizer such that the therapeutic agent has degraded by not more than 5% after 2 years (which may be stored at about 20° C. to about 25° C., and relative humidity in the range of 20% to 65%) when the composition is used to fill the lumen of a structural element of a medical device, such as a stent. In other embodiments, the composition includes a therapeutic agent and a sufficient amount of a metal ion stabilizer such that the therapeutic agent has degraded by not more than 4.5%, not more than 4%, not more than 3.5%, or not more than 2% after 2 years when the composition is used to fill the lumen of a structural element of a medical device, such as a stent. In still other embodiments, the composition includes a therapeutic agent and a sufficient amount of a metal ion stabilizer such that the therapeutic agent has not degraded by more than 5% after 18 months, after 12 months, after 9 months, or after 6 months when the composition is used to fill the lumen of a structural element of a medical device, such as a stent. The term "after 2 years" refers to the date that is 2 years after the composition is filled into the lumen of a structural element of a medical device such as a stent, and after sterilization and packaging. After filling, the medicated stent is then sterilized by a terminal sterilization process, such as, but not limited to, ethylene oxide sterilization, packaged in an inert gas atmosphere, and aged under ambient conditions (which may be about 20° C. to about 25° C., and relative humidity in the range of 20% to 65%).

The metal ion stabilizer may be combined with the drug at a molecular level for the highest efficacy. Thus, combining a therapeutic agent in a powder form with a metal ion stabilizer in a powder form and then filling the lumen of the device, such as a stent, with the powder combination may not be the most effective means of protecting the therapeutic agent from the effects of metal ions. Preferably, the therapeutic agent, and the metal ion stabilizer, are dissolved, dispersed, or a combination of dissolved and dispersed in a solvent to form a combination for filling. In some embodiments the therapeutic agent, and the metal ion stabilizer, are dissolved in the solvent, and in other embodiments, the therapeutic agent, and the metal ion stabilizer are dispersed in the solvent, or at least partially dispersed in the solvent. In some embodiments, the therapeutic agent is dissolved in the solvent while the metal ion stabilizer is dispersed, or at least partially dispersed in the solvent. In still other embodiments, the therapeutic agent is dispersed, or at least partially dispersed in the solvent, and the metal ion stabilizer is dissolved in the solvent. The lumen of the structural element of the stent is filled with the combination for filling via any means, and the solvent is then removed, or substantially removed (less than 5 wt % in the composition filling the lumen) by any means. In some embodiments, the therapeutic agent is dissolved, dispersed, or a combination of dissolved and dispersed in one solvent, and the metal ion stabilizer is dissolved, dispersed, or a combination of dissolved and dispersed in another solvent (which may be the same as or different from the solvent used for the therapeutic agent) and the two solvent combinations may be used to fill the lumen sequentially or may be combined together before filling, during filling, or both before and during filling of the lumen. In still other embodiments, the metal ion stabilizer could be dissolved in one solvent, such as a polar solvent, for example, water, and the therapeutic agent is dissolved in an organic solvent, such as acetone. Metal ion stabilizer solution can be filled into the stent lumen first, followed by the therapeutic agent solution, or vice versa. Solvent removal could proceed after both agents are filled into the stent lumen. Solvent removal could also proceed after one agent is filled. Non-limiting examples of filling include injection at room temperature (about 20° C. to about 25° C.), injection at an elevated temperature such as between 30° C. and 75° C., or injection at a temperature below room temperature, such as between −10° C. and 10° C. Other non-limiting examples of methods of filling include immersion, immersion followed by drawing a vacuum, and direct dispensing. Non-limiting examples of solvent removal include lyophilization, removal by evaporation at room temperature (about 20° C. to about 25° C.), evaporation at an elevated temperature (>about 30° C., such as for example between 32° C. and 120° C.), evaporation under vacuum (below 1 atmosphere pressure, for example not more than 200 Torr, or not more than 20 Torr, but not less than 0.01 Torr), and any combination thereof.

The choice of solvent used to load the therapeutic agent into the lumen of a structural element of a stent may also affect the number of metal ions which are in contact with the therapeutic agent. As an example, a more polar solvent, such as methanol, may be able to solubilize more residual metal salts, thus increasing the potential for contact with the therapeutic agent. In contrast, it is believed that a very nonpolar solvent, for example and without limitation, hexane, would solubilize fewer metal ions. Thus, in some embodiments, a nonpolar solvent may be used. In some embodiments a solvent with a solubility parameter of less than or equal to 16 $(MPa)^{1/2}$ may be used. Non-limiting examples of non-polar solvents that may be used, individually or in combination, n-hexane, n-heptane, octane, decane, ethyl ether, propyl ether, diisopropyl ether, butyl ether, and diisobutyl ketone.

Another means of combining the metal ion stabilizer and the therapeutic agent is by melting the therapeutic agent, and potentially also melting the metal ion stabilizer, and combining the metal ion stabilizer with the melted therapeutic agent. The combination, with the therapeutic agent still melted, may be used to fill the lumen of a structural element of a stent.

Once the structural elements of a medical device, such as the strut tubes of a stent, have been filled with a composition and some openings optionally sealed, the outer surface, or at least a portion of the outer surface, of a stent having hollow struts may be coated. The coating may be polymeric, metallic, glass, ceramic, other material, or any combination thereof. In preferred embodiments, the coating includes a polymer. A typical coating process involves dissolving and/or dispersing the coating materials, such as, for example, a polymer, optionally with other excipients, a therapeutic agent, or a combination thereof, in a solvent to form a coating solution, and disposing the coating solution over the outer surface of the stent by procedures such as spraying, brushing, wiping or directly depositing the solution onto the surface of the stent. The solution may be applied by immersing the stent in the solution. Non-limiting examples of other processes of applying a coating, which may or may not include a solvent, are plasma deposition processes, electrostatic deposition processes, and other dry powder application processes. Such coating procedures are well-known in the art. Any coating process may be executed in such a manner as to prevent or limit to a minimal amount (for example, not more than 25 wt %) removal of the composition within the lumens of the strut tubes.

The coating may comprise a polymer, a therapeutic agent, another material, or a combination thereof. If a therapeutic agent is included in the coating, the therapeutic agent may be the same as, or different from, the therapeutic agent of the composition in the lumens of the strut tubes. In some embodiments, the therapeutic agent of the composition within the strut tubes may differ from the therapeutic agent in the coating only in that the one is a salt, hydrate, or polymorph of the other, or the two are different salts or hydrates of the same chemical entity. In other embodiments the therapeutic agent in the composition of the strut tubes may be different chemical entities, that is the chemical entity exhibiting the pharmacological activity is different.

In preferred embodiments, the coating comprises a polymer, which may be a biostable polymer, a biodegradable polymer, or a combination thereof. The coating may comprise a primer layer free of, or essentially free of (less than 5 wt % or less than 2 wt %), therapeutic agents. The coating may also include other excipients. Non-limiting examples of such excipients include lubricating agents, fillers, plasticizing agents, surfactants, diluents, mold release agents, agents which act as therapeutic active agent carriers, binders, anti-tack agents, anti-foaming agents, viscosity modifiers, anti-oxidants, stabilizers, potentially residual levels of solvents, and potentially any other agent which aids in, or may be desirable in, the processing of the material, and/or may be useful or desirable as a component of the final product. Surfactants may be used for the preparation of a dispersion of polymer and/or therapeutic agent in a solvent or fluid.

Embodiments of the present invention encompass coatings in which the coating layer, or materials included in the coating layer such as a polymer and/or therapeutic agents, are not covalently bound or chemically bound to the surface to which the coating is applied (the substrate surface, or a previously applied coating layer). Embodiments also encompass stents and devices with a coating formed by the application of one or more layers as described above, and include stents and devices with coatings in which one or more materials migrate from one layer to another either during the coating application process, after the coating application process has been completed, or both. In some embodiments, the therapeutic agent in the lumen may migrate into the coating during the coating application process, after the coating application process, or both.

Examples of polymers that may be used in the various embodiments of the present invention include, without limitation, poly(N-acetylglucosamine) (chitin); chitosan; poly(hydroxyvalerate); poly(hydroxybutyrate), poly(hydroxybutyrate-co-valerate); poly(3-hydroxybutyrate), poly(4-hydroxybutyrate); poly(3-hydroxyvalerate); poly(hydroxybutyrate-co-valerate); polyorthoesters; polyanhydrides; homopolymers of any of the following and random and block copolymers of any combination of the following, and also including block copolymers with one block being polyethylene glycol and at least one other block being a homopolymer or a random copolymer of any combination of the following: D-lactic acid, L-lactic acid, DL-lactic acid, meso-lactide, caprolactone (including but not limited to, ε-caprolactone), glycolide (glycolic acid), trimethylene carbonate, valeroactone, γ-undecalactone, β-methyl-δ-valerolactone, and hydroxycarboxylic acids (including, but not limited to, 3-hydroxybutyric acid, 4-hydroxybutyric acid, 3-hydroxyvaleric acid, 4-hydroxyvaleric acid, 5-hydroxyvaleric acid, dimethylglycolic acid, β-hydroxypropanic acid, α-hydroxybutyric acid, α-hydroxycaproic acid, β-hydroxycaproic acid, γ-hydroxycaproic acid, δ-hydroxycaproic acid, δ-hydroxymethylcaproic acid, ε-hydroxycaproic acid, and ε-hydroxymethylcaproic acid); poly(glycolide-co-caprolactone) polymers; poly(thioesters); polyethylene amide; polyester amide polymers; polyethylene acrylate; acrylate and methacrylate polymers; co-poly(ether-esters) (e.g., PEO/PLA); polyphosphazenes; biomolecules (e.g., fibrin, fibrinogen, cellulose, starch, collagen and hyaluronic acid); polyurethanes; silicones; polyesters; polyolefins; polyisobutylene and ethylene-alphaolefin copolymers; acrylic polymers; vinyl halide polymers and copolymers (e.g., polyvinyl chloride); polyvinyl ethers (e.g., polyvinyl methyl ether); polyvinylidene halides (e.g., polyvinylidene chloride); polyacrylonitrile; polyvinyl ketones; polyvinyl aromatics (e.g., polystyrene); polyvinyl esters (e.g., polyvinyl acetate); acrylonitrile-styrene copolymers; ABS resins; polyamides (e.g., Nylon 66 and polycaprolactam); polycarbonates; polyoxymethylenes; polyimides; polyethers; rayon; rayon-triacetate; cellulose and derivatives thereof and copolymers thereof (including without limitation cellulose acetate, cellulose butyrate, cellulose acetate butyrate, cellophane, cellulose nitrate, cellulose propionate, cellulose ethers, and carboxymethyl cellulose); and any copolymers and any blends in any proportions of the aforementioned polymers.

Additional representative examples of polymers for use in the various embodiments of the present invention include, without limitation, ethylene vinyl alcohol copolymer (commonly known by the generic name EVOH or by the trade name EVAL™); poly(butyl methacrylate); poly(vinylidene fluoride-co-hexafluoropropylene) (e.g., SOLEF® 21508, available from Solvay Solexis PVDF of Thorofare, N.J.); polyvinylidene fluoride (otherwise known as KYNAR™, available from Atofina Chemicals of Philadelphia, Pa.); poly(tetrafluoroethylene-co-hexafluoropropylene-co-vinylidene fluoride); ethylene-vinyl acetate copolymers; and polyethylene glycol; and copolymers and combinations thereof.

As used herein, the terms poly(D,L-lactide) (PDLL), poly(L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

Any of the above polymers or materials specifically listed may be used individually, in combination with any other polymer, in combination with any other material, or in combination with any other polymer and any other material listed herein, and may be used in combination at any proportions.

Various embodiments of the current invention encompass both uncross-linked and cross-linked polymers, branched and unbranched polymers, and dendritic polymers. In preferred embodiments, the polymers used may be uncross-linked or not crosslinked. With respect to the metal ion stabilizer, as well as other excipients, it is preferable that these compounds are biocompatible and may be released into the body with the therapeutic agent.

Embodiments of the present invention include methods of using any of the medical devices described herein to treat, prevent, diagnose, or a combination thereof, various conditions or disorders in a patient (animal, including human) in need of treatment, prevention, or diagnosis of a condition or disorder. Examples of such conditions or disorders include, but are not limited to, benign pancreatic disease, coronary artery disease, carotid artery disease, peripheral arterial disease, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction, and combinations thereof.

The medical devices, such as stents, of the various embodiments of the invention can be used in, without limitation, neuro, carotid, coronary, pulmonary, aorta, renal, biliary, iliac, femoral and popliteal, as well as other peripheral vasculatures, and in other bodily lumens such as the urethra or bile duct.

All publications, patents, and patent applications cited in this specification are herein incorporated by reference as if each individual publication, patent, or patent application were specifically and individually indicated to be incorporated by reference.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims where such dependency would be logically consistent).

What is claimed is:

1. A medical device, the device comprising:
   a device body comprising at least one structural element, the structural element comprising a lumen and at least one opening to access the lumen; and
   a composition within the lumen, the composition comprising a therapeutic agent, and a metal ion stabilizer;
   wherein the at least one structural element has walls, the walls forming an interior surface and the lumen being surrounded by the interior surface;
   wherein the composition comprises at least 0.1 μg of the metal ion stabilizer/cm² of the interior surface surrounding the lumen and not more than 15 μg metal of the ion stabilizer/cm² of the interior surface surrounding the lumen;
   and
   wherein the medical device is a stent.

2. The medical device of claim 1, wherein the metal ion stabilizer comprises a metal chelator.

3. The medical device of claim 1, wherein the metal ion stabilizer comprises a precipitation agent.

4. The medical device of claim 1, wherein the device body is biostable.

5. The medical device of claim 1, wherein the device body is formed of a biostable metal selected from the group consisting of 316L stainless steel, CoNi MP35N, CoCr L-605, elgiloy, nitinol, FePtCr, and combinations thereof.

6. The medical device of claim 1, wherein the interior surface of the at least one structural element of the stent body is not electropolished, or a degree of electropolishing of the interior surface of the at least one structural element is less than the outer surface of the stent.

7. The medical device of claim 1, wherein the therapeutic agent belongs to a macrolide lactone family and the therapeutic agent contains a triene moiety.

8. The medical device of claim 1, wherein the therapeutic agent is selected from the group consisting of rapamycin, everolimus, Biolimus A9, umirolimus, ridaforolimus, tacrolimus, temsirolimus, pimecrolimus, novolimus, merilimus, zotarolimus, 40-O-(3-hydroxypropyl)rapamycin, 40-O-[2-(2-hydroxy)ethoxy]ethyl-rapamycin, 40-O-tetrazolylrapamycin, 40-epi-(N1-tetrazolyl)-rapamycin, and combinations thereof.

9. The medical device of claim 1, wherein the metal ion stabilizer comprises a chelator selected from the group consisting of ethylene diamine tetraacetic acid (EDTA), calcium disodium EDTA, EDTA with a counterion of potassium, EDTA with a counterion of ammonium, EDTA with a counterion of a quaternary ammonium compound, 2,3-dimereapto-1-propanesulfonic acid, dimercaptosuccinic acid, dimercaprol, desferrioxamine mesylate, alpha lipoic acid, nitrilotriacetate, penicillamine, thiamine tetrahydrofurfiuyl disulfide, deferiprone, deferasirox, kojic acid, bisphosphonates, 3-hydroxy-4-pyridinecarboxylic acid, 4-hydroxy-3-pyridinecarboxylic acid, 1,6-Dimethyl-4-hydroxy-3-pyridinecarboxylic acid, 4-hydroxy-2-methyl-3-pyridinecarboxylic acid, and combinations thereof.

10. The medical device of claim 1, wherein the metal ion stabilizer comprises a chelator selected from the group consisting of sodium ascorbate, desferrioxamine, malic acid, citric acid, succinic acid, sodium, calcium, and magnesium salts of malic acid, citric acid, and succinic acid, feralex-G, clioquinol, curcumin, epigallocatechin, 3-hydroxy-4-pyridinone, 3-hydroxy-4-pyridinecarboxylic acid, 4-hydroxy-3-pyridinecarboxylic acid, 1,6-Dimethyl-4-hydroxy-3-pyridinecarboxylic acid, 4-hydroxy-2-methyl-3-pyridinecarboxylic acid, and combinations thereof.

11. The medical device of claim 1, wherein the metal ion stabilizer comprises a precipitation agent selected from the group consisting of stearic acid, lauric acid, capric acid, and caprylic acid, and sodium, calcium, and magnesium salts thereof, and combinations thereof.

12. The medical device of claim 1, wherein a combination of the therapeutic agent and the metal ion stabilizer comprises at least 50 wt % of the composition, at least 70 wt % of the composition, or at least 90 wt % of the composition.

13. The medical device of claim 1, wherein at least 90% of the volume of the lumen is filled with the composition.

14. The medical device of claim 1, wherein the metal ion stabilizer is selected from the group consisting of 2,3-dimereapto-1-propanesulfonic acid, dimercaptosuccinic acid, dimercaprol, desferrioxamine mesylate, alpha lipoic acid, nitrilotriacetate, penicillamine, thiamine tetrahydrofurfiuyl disulfide, deferiprone, deferasirox, kojic acid, bisphosphonates, 3-hydroxy-4-pyridinecarboxylic acid, 4-hydroxy-3-pyridinecarboxylic acid, 1,6-Dimethyl-4-hydroxy-3-pyridinecarboxylic acid, 4-hydroxy-2-methyl-3-pyridinecarboxylic acid, desferrioxamine, succinic acid, sodium, calcium, and magnesium salts of succinic acid, feralex-G, clioquinol, curcumin, epigallocatechin, stearic acid, lauric acid, capric acid, and caprylic acid, and sodium, calcium, and magnesium salts of stearic acid, lauric acid, capric acid, and caprylic acid, and combinations thereof.

15. The medical device of claim 1, wherein the at least one opening comprises one or more side openings to access the lumen and allow the therapeutic agent to be released from the lumen, and the side openings one or more being only on the abluminal side of the medical device.

16. A stent comprising:
   a plurality of interconnected structural elements comprising a metallic material, wherein at least some of the structural elements are annular and comprise an interior lumen;
   and
   a therapeutic agent and an additive disposed within the interior lumen(s);
   wherein an inner surface of the annular structural element(s) is susceptible to release of metal ions which are capable of degrading the therapeutic agent;
   wherein the additive is for protecting the therapeutic agent from degradation by the metal ions by rendering the metal ions unable to interact with the therapeutic agent;
   wherein the additive is present at an amount of at least 0.1 μg/cm² of the inner surface and not more than 15 μg/cm² of the inner surface; and
   wherein the additive is selected from the group consisting of 2,3-dimereapto-1-propanesulfonic acid, dimercaptosuccinic acid, dimercaprol, desferrioxamine mesylate, alpha lipoic acid, nitrilotriacetate, thiamine tetrahydrofurfiuyl disulfide, deferiprone, deferasirox, kojic acid, bisphosphonates, 3-hydroxy-4-pyridinecarboxylic acid, 4-hydroxy-3-pyridinecarboxylic acid, 1,6-Dimethyl-4-hydroxy-3-pyridinecarboxylic acid, 4-hydroxy-2-methyl-3-pyridinecarboxylic acid, desferrioxamine, succinic acid, sodium, calcium, and magnesium salts of succinic acid, feralex-G, clioquinol, epigallocatechin, 3-hydroxy-4-pyridinone, stearic acid, lauric acid, capric acid, and caprylic acid, and sodium, calcium, and magnesium salts of stearic acid, lauric acid, capric acid, and caprylic acid, and combinations thereof.

17. The stent of claim 16, wherein the therapeutic agent is degraded by not more than 5 wt % at the end of the shelf-life of the stent, and wherein the shelf-life of the stent is at least 6 months, at least 9 months, at least 12 months, at least 18 months, or at least 24 months.

18. The stent of claim 16, wherein the additive is selected from the group consisting of 2,3-dimereapto-1-propanesulfonic acid, dimercaptosuccinic acid, dimercaprol, desferrioxamine mesylate, alpha lipoic acid, nitrilotriacetate, thiamine tetrahydrofurfiuyl disulfide, deferiprone, deferasirox, kojic acid, 3-hydroxy-4-pyridinecarboxylic acid, 4-hydroxy-3-pyridinecarboxylic acid, 1,6-Dimethyl-4-hydroxy-3-pyridinecarboxylic acid, 4-hydroxy-2-methyl-3-pyridinecarboxylic acid, desferrioxamine, feralex-G, clioquinol, epigallocatechin, and combinations thereof.

19. The stent of claim 16, wherein the additive comprises kojic acid.

20. A stent comprising:
a plurality of interconnected structural elements comprising a metallic material, wherein at least some of the structural elements are annular and comprise an interior lumen;
and
a therapeutic agent and an additive disposed within the interior lumen(s);
wherein an inner surface of the annular structural element(s) is susceptible to release of metal ions which are capable of degrading the therapeutic agent;
wherein the additive is for protecting the therapeutic agent from degradation by the metal ions by rendering the metal ions unable to interact with the therapeutic agent;
wherein the additive is present at an amount of at least 0.1 $\mu g/cm^2$ of the inner surface and not more than 15 $\mu g/cm^2$ of the inner surface; and
wherein the annular structural elements comprising the interior lumen are tubes formed from tube stock with the interior lumen of essentially uniform cross-sectional area and the tubes comprising one or more side openings to access the interior lumen and allow the therapeutic agent to be released from the interior lumen, and the side openings have a cross-sectional area of not more than 10% of the cross-sectional area of the lumen of the tube stock from which the annular structural element was formed.

21. A method comprising:
providing a medical device having a structural element, the structural element comprising a lumen and at least one opening to access the lumen;
filling the lumen of the structural element with a composition comprising a therapeutic agent and a metal ion stabilizer;
wherein the at least one structural element has walls, the walls forming an interior surface, and the lumen being surrounded by the interior surface;
wherein the composition comprises at least 0.1 µg of the metal ion stabilizer/cm$^2$ of the interior surface surrounding the lumen and not more than 15 µg of the metal ion stabilizer/cm$^2$ of the interior surface surrounding the lumen;
and
wherein the medical device is a stent.

22. The medical of claim 21, wherein the metal ion stabilizer comprises a metal chelator.

23. The medical of claim 21, wherein the metal ion stabilizer comprises a precipitation agent.

24. The method of claim 21, wherein filling the lumen comprises forming a filling composition by executing a first operation comprising dissolving, dispersing, or both dissolving and dispersing the therapeutic agent in a solvent and dissolving, dispersing, or both dissolving and dispersing the metal ion stabilizer in the solvent, executing a second operation comprising placing the filling composition into the lumen, and executing a third operation comprising removing the solvent.

25. The method of claim 24, wherein the solvent comprises a solvent selected from the group consisting of n-hexane, n-heptane, octane, decane, ethyl ether, propyl ether, diisopropyl ether, butyl ether, diisobutyl ketone, and combinations thereof.

* * * * *